US010687696B2

(12) United States Patent
Kinouchi et al.

(10) Patent No.: US 10,687,696 B2
(45) Date of Patent: Jun. 23, 2020

(54) ENDOSCOPE SYSTEM WITH COMMUNICATION MODE STABILIZING UNIT

(71) Applicant: OLYMPUS CORPORATION, Tokyo (JP)

(72) Inventors: Hideaki Kinouchi, Musashino (JP); Tsutomu Urakawa, Hachioji (JP); Susumu Kawata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 342 days.

(21) Appl. No.: 15/722,052

(22) Filed: Oct. 2, 2017

(65) Prior Publication Data

US 2018/0035877 A1 Feb. 8, 2018

Related U.S. Application Data

(63) Continuation of application No. PCT/JP2016/055195, filed on Feb. 23, 2016.

(30) Foreign Application Priority Data

Apr. 23, 2015 (JP) .................................. 2015-088514

(51) Int. Cl.
*A61B 1/05* (2006.01)
*A61B 1/00* (2006.01)
(Continued)

(52) U.S. Cl.
CPC .................. *A61B 1/05* (2013.01); *A61B 1/00* (2013.01); *A61B 1/00013* (2013.01);
(Continued)

(58) Field of Classification Search
CPC ............ A61B 1/00013; A61B 1/00117; A61B 1/00165; A61B 1/00167
See application file for complete search history.

(56) References Cited

U.S. PATENT DOCUMENTS 4,421,383 A * 12/1983 Carlsen .................... G02B 6/32
385/72
4,563,057 A * 1/1986 Ludman .................. G02B 6/32
385/74
(Continued)

FOREIGN PATENT DOCUMENTS

CN 101988977 A 3/2011
CN 102946045 A 2/2013
(Continued)

OTHER PUBLICATIONS

International Search Report dated May 17, 2016 issued in PCMP2016/055195.
(Continued)

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

An endoscope system includes: an image sensor; a transmission module; a first optical fiber; a first optical connector; a second optical connector; a communication mode stabilizing unit configured to smooth an optical beam; a second optical fiber having a core diameter larger than a core diameter of the first optical fiber; a reception module; a first correction optical system including a first lens and configured to increase a beam diameter of an optical signal output from an end of the first optical fiber, and a second lens configured to convert the optical signal whose beam diameter is increased by the first lens into parallel light; and a second correction optical system. The second optical fiber is a step index optical fiber, and the communication mode stabilizing unit smoothes the optical beam by using a larger area of a core of the first optical fiber.

5 Claims, 4 Drawing Sheets

(51) Int. Cl.
*G02B 6/32* (2006.01)
*G02B 23/24* (2006.01)
*A61B 1/04* (2006.01)
*A61B 1/06* (2006.01)
*G02B 6/42* (2006.01)

(52) U.S. Cl.
CPC ............ *A61B 1/00165* (2013.01); *A61B 1/04* (2013.01); *A61B 1/0676* (2013.01); *G02B 6/32* (2013.01); *G02B 23/24* (2013.01); *A61B 1/00117* (2013.01); *G02B 6/4206* (2013.01); *G02B 6/4256* (2013.01)

(56) References Cited

U.S. PATENT DOCUMENTS

| | | | | |
|---|---|---|---|---|
| 5,039,193 | A | * | 8/1991 | Snow ..................... G02B 6/262 385/25 |
| 5,293,438 | A | * | 3/1994 | Konno ................. G02B 6/2552 385/35 |
| 5,847,416 | A | | 12/1998 | Ohta et al. |
| 8,596,880 | B2 | * | 12/2013 | Wu ....................... G02B 6/3825 385/74 |
| 10,386,580 | B2 | * | 8/2019 | Suzuki ................. G02B 6/4207 |
| 2001/0017961 | A1 | * | 8/2001 | Kittaka ................ G02B 6/2937 385/34 |
| 2007/0230517 | A1 | * | 10/2007 | Matsuda ............ B23K 26/0643 372/6 |
| 2010/0141732 | A1 | * | 6/2010 | Sasaki ....................... B41J 2/46 347/255 |
| 2011/0026885 | A1 | | 2/2011 | Lin |
| 2014/0376860 | A1 | | 12/2014 | Mitsui et al. |

FOREIGN PATENT DOCUMENTS

| | | | | |
|---|---|---|---|---|
| JP | S56-146103 | A | | 11/1981 |
| JP | S59-036213 | A | | 2/1984 |
| JP | H01-234804 | A | | 9/1989 |
| JP | H01234804 | A | * 9/1989 | ............... G02B 6/26 |
| JP | H04-101508 | U | | 9/1992 |
| JP | H05-288956 | A | | 11/1993 |
| JP | H09-172161 | A | | 6/1997 |
| JP | 2010-101669 | A | | 5/2010 |
| JP | 2010-194037 | A | | 9/2010 |
| JP | 2010194037 | A | * 9/2010 | ......... A61B 1/00013 |
| JP | 2011-152369 | A | | 8/2011 |
| JP | 2013-156337 | A | | 8/2013 |

OTHER PUBLICATIONS

Japanese Notification of Reasons for Refusal dated Feb. 2, 2017 issued in JP 2016-567940.
Chinese Office Action dated Dec. 24, 2019 in Chinese Patent Application No. 201680020376.6.

* cited by examiner

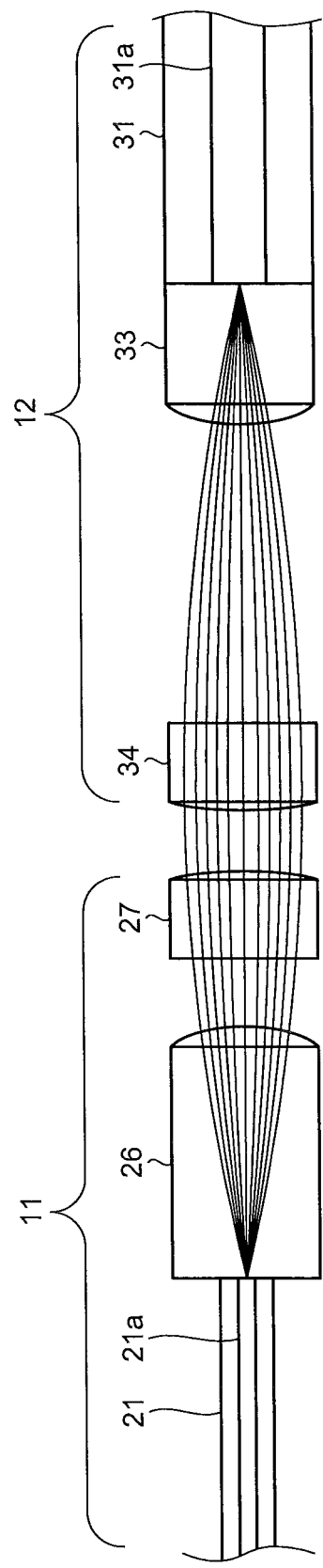
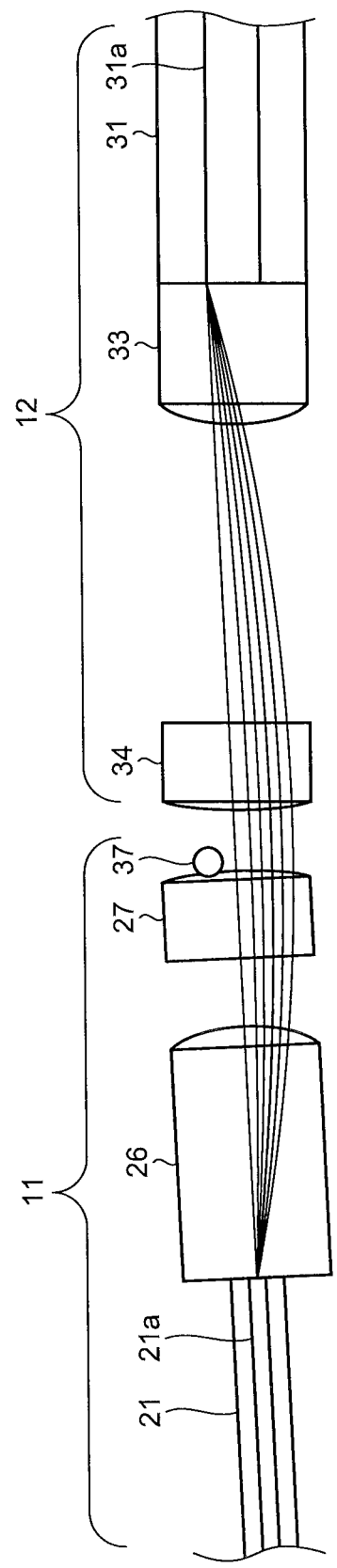
FIG.3A
FIG.3B

ENDOSCOPE SYSTEM WITH COMMUNICATION MODE STABILIZING UNIT

CROSS REFERENCES TO RELATED APPLICATIONS

This application is a continuation of PCT International Application No. PCT/JP2016/055195 filed on Feb. 23, 2016 which claims the benefit of priority from Japanese Patent Application No. 2015-088514 filed on Apr. 23, 2015, the entire contents of which are incorporated herein by reference.

BACKGROUND

The present disclosure relates to an endoscope system.

Endoscope systems are used for observation of organs of subjects such as patients in the medical field. An endoscope system includes: an endoscope including an insertion part provided with an image sensor at a distal end, the insertion part having a flexible elongated shape and being inserted into a body cavity of a subject; an information processing device connected with the insertion part via a cable and a connector and configured to perform image processing on in-vivo images captured by the image sensor; and a display device configured to display the in-vivo images, for example.

In recent years, image sensors with large numbers of pixels enabling observation with clearer image have been developed, and it has been considered to use the image sensors with large numbers of pixels for an endoscope. In addition, there are demands for reducing the diameter of the insertion part in view of facilitating introduction into a subject. Furthermore, a transmission system using optical fibers and optical waveguides has been employed in endoscope systems for high-speed and large-capacity signal transmission between an image sensor and an information processing device while achieving reduction in diameter of the insertion parts.

As such a technique, an endoscope system in which an imaging unit converts an imaging signal into an optical signal by an E/O converter, and the optical signal is transmitted by an optical fiber and output to an O/E converter in a processor, is disclosed (for example, refer to JP 2010-194037 A).

In addition, an endoscope system including a light source device capable of outputting a plurality of kinds of laser light, in which holder aligning unit for aligning the optical axes of a plurality of optical fibers, which transmit laser light, is provided in an optical connector for connecting the optical fibers is disclosed (for example, refer to JP 2011-152369 A).

SUMMARY

An endoscope system according to one aspect of the present disclosure may include: an image sensor configured to image a subject; a transmission module including a first photoelectric element configured to convert an imaging signal output from the image sensor into an optical signal and output the optical signal; a first optical fiber configured to transmit the optical signal output from the first photoelectric element; a first optical connector configured to hold an end of the first optical fiber connected with the first photoelectric element, the end being opposite to an end connected with the first photoelectric element; a second optical connector removably connected with the first optical connector; a communication mode stabilizing unit provided between the transmission module and the first optical connector and configured to smooth an optical beam transmitted by the first optical fiber; a second optical fiber configured to transmit the optical signal output from the first optical fiber, the second optical fiber being held by the second optical connector and having a core diameter larger than a core diameter of the first optical fiber; a reception module including a second photoelectric element configured to convert the optical signal transmitted by the second optical fiber into an electrical signal and output the electrical signal; a first correction optical system including a first lens incorporated in the first optical connector and configured to increase a beam diameter of the optical signal output from the end of the first optical fiber, and a second lens configured to convert the optical signal whose beam diameter is increased by the first lens into parallel light; and a second correction optical system incorporated in the second optical connector and configured to collect the optical signal output from the first correction optical system, wherein the second optical fiber is a step index optical fiber having a refractive index discontinuously changing only at a core-cladding interface, and the communication mode stabilizing unit smoothes the optical beam transmitted to the first optical fiber by using a larger area of a core of the first optical fiber, and input the optical bean into the second optical fiber that is the step index optical fiber.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3A and FIG. 3B are diagrams illustrating transmission of an optical signal according to the embodiment of the present disclosure.

DETAILED DESCRIPTION

Figure 1:
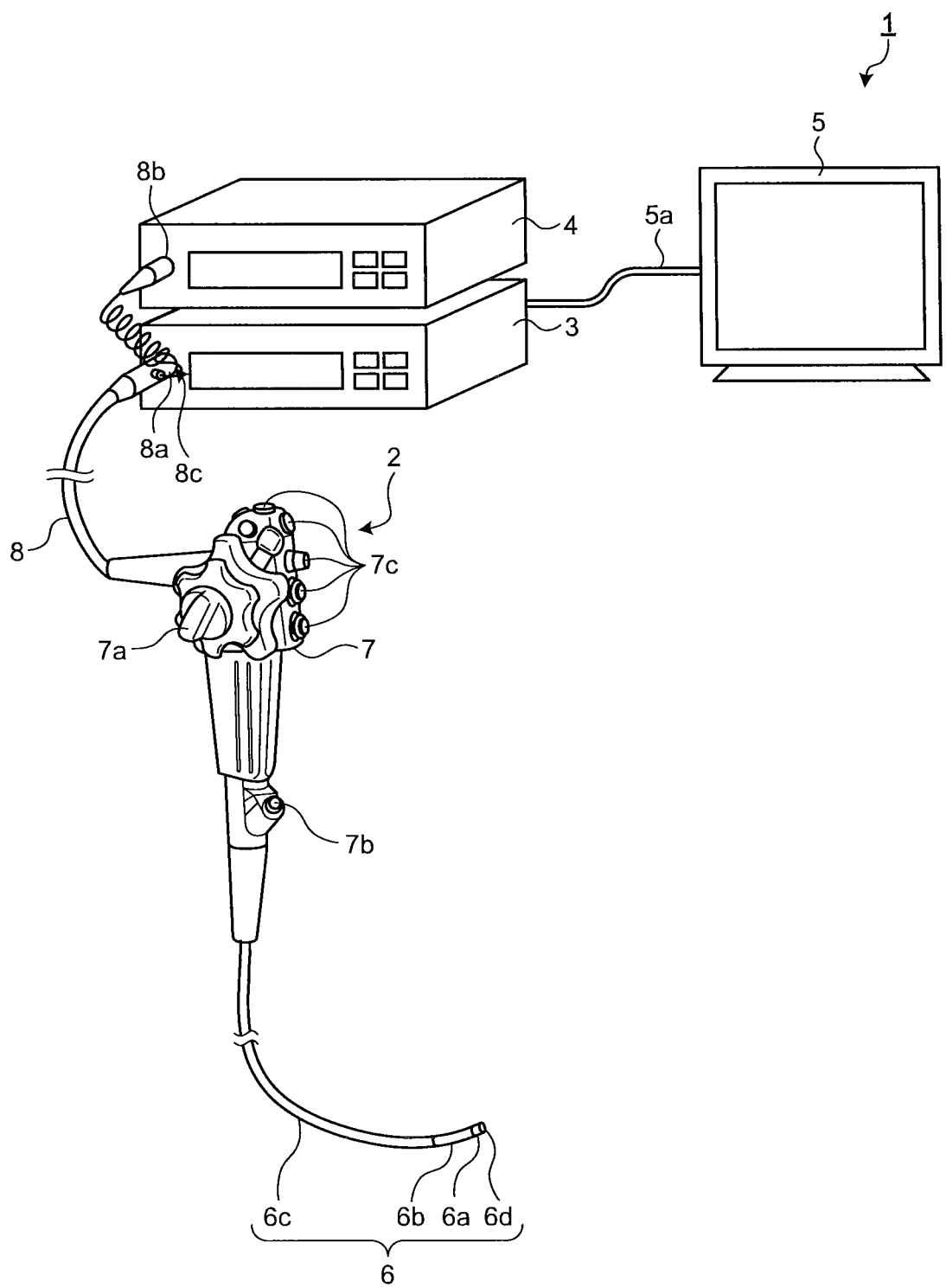
FIG. 1 is a schematic diagram illustrating a schematic configuration of an endoscope system according to an embodiment of the present disclosure.

In the description below, an endoscope system, which is a mode for carrying out the present disclosure (hereinafter referred to as an "embodiment"), will be described. Note that the present disclosure is not limited to the embodiment. In depiction of the drawings, the same components will be designated by the same reference numerals.

Embodiment

Figure 2:
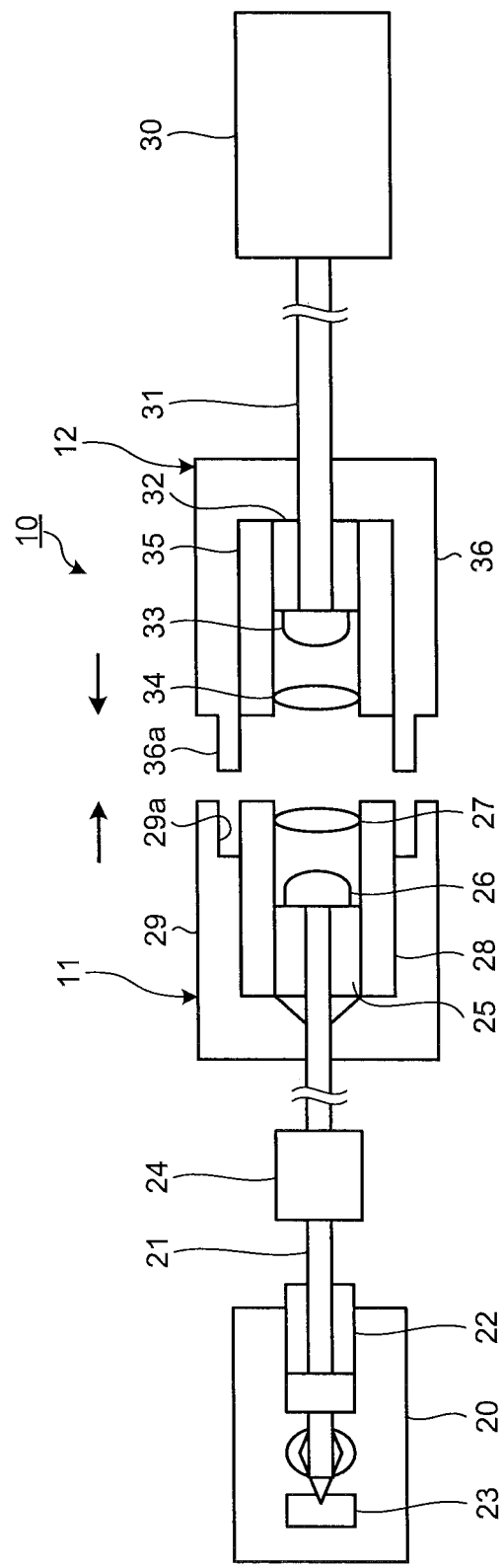
FIG. 2 is a schematic diagram illustrating a schematic configuration of an optical connector to for use in the endoscope system according to the embodiment of the present disclosure.

FIG. 1 is a schematic diagram illustrating a schematic configuration of an endoscope system according to an embodiment of the present disclosure. FIG. 2 is a schematic diagram illustrating a schematic configuration of an optical connector for use in the endoscope system according to the embodiment of the present disclosure. FIG. 2 illustrates a state in which a first optical connector 11 and a second optical connector 12 are disconnected from each other.

As illustrated in FIGS. 1 and 2, an endoscope system 1 according to the embodiment includes an endoscope 2 to be introduced into a subject and configured to capture an inside of a body of the subject and generate an image signal of the inside of the subject, an information processing device 3 (external processor) configured to perform predetermined image processing on the image signal captured by the endoscope 2 and control the respective components of the endoscope system 1, a light source device 4 configured to generate illumination light for the endoscope 2, and a display device 5 configured to display an image corresponding to the image signal resulting from image processing performed by the information processing device 3.

The endoscope 2 includes an insertion part 6 to be inserted into the subject, an operating unit 7, which is provided adjacent to a proximal end portion of the insertion part 6 and which is to be gripped by an operator, and flexible universal cord 8 extending from the operating unit 7.

The insertion part 6 is constituted by an illumination fiber (light guide cable), an electric cable, an optical fiber, and the like. The insertion part 6 has a distal end portion 6a incorporating an image sensor, a bending portion 6b, which is freely bendable and constituted by a plurality of bending pieces, and a flexible tube portion 6c, which is flexible and provided on the proximal end side of the bending portion 6b. The distal end portion 6a is provided with an illumination portion for illuminating the inside of the subject via an illumination lens, an observation portion for capturing the inside of the subject, an aperture 6d through which a channel for a treatment tool communicates, and an air/water nozzle (not illustrated).

At the distal end portion 6a, the image sensor located at an image forming position of an optical system for light collection and configured to receive light collected by the optical system, perform photoelectric conversion on the light into an electrical signal and perform predetermined signal processing on the electrical signal, and a transmission module 20 having a light emitting element 23 configured to convert an electrical signal containing image information input form the image sensor into an optical signal and transmit the optical signal to the information processing device 3 are arranged. The transmission module 20 holds and fixes an end of a first optical fiber 21, which transmits an optical signal output from the light emitting element 23, with a ferrule 22 therebetween.

The operating unit 7 includes a bending nob 7a for bending the bending portion 6b upward, downward, leftward, and rightward, treatment tool insertion part 7b through which a treatment tool such as living body forceps or a laser knife is inserted into the body cavity of a subject, and a plurality of switches 7c for operation of peripheral devices such as the information processing device 3, the light source device 4, an air supply device, a water supply device, and a gas supply device. A treatment tool inserted through the treatment tool insertion part 7b passes through a treatment tool channel formed thereinside and comes out from the aperture 6d at the distal end of the insertion part 6.

The universal cord 8 is constituted by an illumination fiber, an electric cable, the first optical fiber 21, and the like. The universal cord 8 branches at the proximal end into one end being a first connector 8a and the other proximal end being an illumination connector 8b. The first connector 8a is removably connected with a second connector 8c of the information processing device 3. The illumination connector 8b is removably connected with the light source device 4. The first connector 8a incorporates the first optical connector 11 for holding the first optical fiber 21, and the second connector 8c incorporates the second optical connector 12 for holding a second optical fiber 31.

The information processing device 3 performs predetermined image processing on an image signal of the inside of the subject captured by an imaging unit at the distal end portion 6a of the endoscope 2. The information processing device 3 controls the respective components of the endoscope system 1 on the basis of various instruction signals transmitted from the switches 7c at the operating unit 7 of the endoscope 2 via the universal cord 8.

The light source device 4 is constituted by a light source that emits light, a condenser lens, and the like. The light source device 4 emits light from the light source, and supplies the light as light for illuminating the inside of the subject to be imaged to the endoscope 2 connected via the illumination connector 8b and the illumination fiber and the first connector 8a of the universal cord 8 under the control of the information processing device 3.

The display device 5 is constituted by a display using liquid crystal or organic electro-luminescence (EL), or the like. The display device 5 displays various information data, including images subjected to the predetermined image processing performed by the information processing device 3, via a video cable 5a. This allows the operator to operate the endoscope 2 while looking at an image (in-vivo image) displayed by the display device 5 to observe a desired position in the subject and determine characteristics.

As illustrated in FIG. 2, an optical connector 10 is constituted by the first optical connector 11 and the second optical connector 12. The first optical connector 11 is a connector on a transmitting side, and includes a ferrule 25 for holding the first optical fiber 21, a lens 26 and a lens 27 for increasing the beam diameter of an optical signal output from the end of the first optical fiber 21 to obtain parallel light, a sleeve 28 for positioning and holding the ferrule 25, the lens 26, and the lens 27, and a casing 29 accommodating the sleeve 28. In the present embodiment, the lens 26 and the lens 27 function as a first correction optical system.

The second optical connector 12 is a connector on a receiving side, and includes a ferrule 32 for holding the second optical fiber 31, a lens 33 and a lens 34 for collecting the optical signal with the increased beam diameter output from the lens 27, a sleeve 35 for positioning and holding the lens 33 and the lens 34, and a casing 36 accommodating the sleeve 35 and the ferrule 32. In the present embodiment, the lens 33 and the lens 34 function as a second correction optical system. The first correction optical system and the second correction optical system are not limited to two lenses but may be constituted by one or three lenses.

An optical fiber having a diameter, which is a core diameter, larger than that of the first optical fiber 21 is used for the second optical fiber 31. The second optical fiber 31 preferably has a core diameter that is 2.5 to 3.5 times the core diameter of the first optical fiber 21. The second optical fiber 31 may be either a graded index (GI) optical fiber having a core refractive index continuously changing quadratically in the radial direction or a step index (SI) optical fiber having a refractive index discontinuously changing only at a core-cladding interface. Alternatively, a multicore fiber including a plurality of cores having approximately the same diameter as the first optical fiber 21 may be used.

A protrusion 36a is formed at a connecting end of the casing 36 on the second optical connector 12 side, and the protrusion 36a is fitted into a recess 29a formed in the casing 29 on the first optical connector 11 side so that the first optical connector 11 and the second optical connector 12 are connected with each other.

The first optical connector 11 and the second optical connector 12 incorporate the first connector 8a and the second connector 8c, respectively, and the first connector 8a is removed from the second connector 8c (the first optical connector 11 is also removed from the second optical connector 12) each time observation with the endoscope 2 is terminated. Repetition of the removal may cause adhesion of dirt to the surfaces of the lens 27 and the lens 34 and misalignment in the fitting of the first optical connector 11 and the second optical connector 12.

FIG. 3A and FIG. 3B are diagrams for explaining transmission of an optical signal according to the embodiment of the present disclosure, in which FIG. 3A illustrates a case in which no fitting misalignment is caused and FIG. 3B illustrates a case in which dust 37 has adhered to the lens 27 and fitting misalignment of the first optical connector 11 and the second optical connector 12 is caused. An optical signal output from a core 21a of the first optical fiber 21 is increased in beam diameter and converted into parallel light by the lens 26 and the lens 27, and input to the lens 34 of the second optical connector 12. The lens 33 and the lens 34 collects the optical signal with the increase beam diameter output from the lens 27, and inputs the optical signal to a core 31a of the second optical fiber 31. While the optical light is collected to substantially the central part of the core 31a of the second optical fiber 31 in FIG. 3A in which no fitting misalignment is caused, the position to which the optical signal is collected is shifted in the case where fitting misalignment is caused as illustrated in FIG. 3B. In the embodiment of the present disclosure, an optical fiber having a core diameter larger than that of the first optical fiber 21 is used for the second optical fiber 31, which allows an optical signal to be input to the core 31a of the second optical fiber 31 even when the position to which the optical signal is collected is shifted to some extent owing to adhesion of dirt or fitting misalignment as in FIG. 3B, and thus allows transmission of an optical signal without causing attenuation of the optical signal.

When optical fibers having the same diameter are used for the first optical fiber 21 and the second optical fiber 31 and when the optical axis of an optical connector is tilted by ±0.2°, the light intensity of an optical signal is attenuated by about 40 to 50%; however, it is confirmed that, when the diameter of the second optical fiber 31 is 2.5 to 3.5 times that of the first optical fiber 21, the light intensity of an optical signal is not attenuated even when the optical axis of the optical connector is tilted by +0.4°.

In addition, a communication mode stabilizing unit 24 for smoothing optical beams is provided in the first optical fiber 21 for transmitting optical signals between the transmission module 20 and the first optical connector 11. The provision of the communication mode stabilizing unit 24 allows transmission of an optical signal by using a larger area of the core of the first optical fiber 21, and the communication mode is stabilized. The communication mode stabilizing unit 24 may employ an SGS type, a mandrel type, a microbend type, or the like. With the SGS type, the communication mode may be easily adjusted. With the mandrel type, no additional mechanism is needed. With the microbend type, removal of higher-order modes is more achieved than the other two types. Any one of these types may be employed depending on the need.

Figure 4:
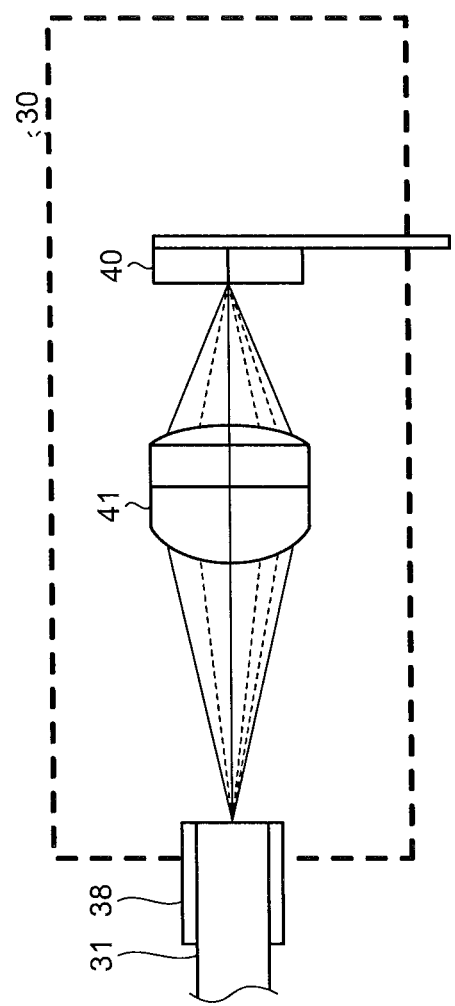
FIG. 4 is a schematic diagram illustrating a schematic configuration of a reception module according to the embodiment of the present disclosure.

A reception module 30 includes a light receiving element configured to convert the optical signal transmitted by the second optical fiber 31 into an electrical signal and output the electrical signal to the information processing device 3. FIG. 4 is a schematic diagram illustrating a schematic configuration of the reception module 30 according to the embodiment of the present disclosure. The reception module 30 includes a casing (not illustrated) for fixing a ferrule 38 for holding the end of the second optical fiber 31, and a lens 41 for collecting the optical signal output from the end of the second optical fiber 31. In the present embodiment, the lens 41 functions as a third correction optical system. The third correction optical system is not limited to one lens as in the present embodiment, but may be constituted by two or three lenses. A third correction optical system constituted by one lens allows miniaturization, and a third correction optical system constituted by two lenses facilitates optical axis alignment. If light collection is difficult with two or less lenses because the core diameter of the second optical fiber 31 is large, the third correction optical system may be constituted by three lenses to enable light collection. The lens configuration may be selected depending on the need. When three lenses are used, a lens adjacent to a light receiving element 40 may be directly connected with the light receiving element 40.

Furthermore, the third correction optical system may be constituted by separate lens or lenses, or may be constituted by an end of the second optical fiber 31 formed in a tapered shape or a hemispherical shape to collect an optical signal. A tapered fiber with an end having a tapered shape or a lensed fiber with an end having a hemispherical shape, a spherical shape or a wedge shape may be used for the second optical fiber 31. Use of a tapered fiber or a lensed fiber reduces the space in which lenses are provided and allows miniaturization of the reception module 30.

While the first optical connector 11 is incorporated in the first connector 8a and the second optical connector 12 is incorporated in the second connector 8c in the embodiment described above, an optical connector may be provided in the operating unit 7. Furthermore, optical connectors may be provided at a plurality of positions in the endoscope system 1, such as in the operating unit 7, the first connector 8a, and the second connector 8c. In a case where a plurality of optical connectors are provided in the endoscope system 1, the diameters of optical fibers used therein are gradually increased from the insertion part 6 side toward the information processing device 3 side, which prevents attenuation of an optical signal.

According to the present disclosure, the core diameter of an optical fiber on a receiving side is larger than that of an optical fiber on a transmitting side, which are connected by an optical connector, which prevents attenuation of an optical signal and allows normal transmission of the optical signal even when dirt is adhered to or fitting misalignment is caused at the optical connector part.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscope system comprising:
an image sensor configured to image a subject;

a transmission module including a light source configured to convert an imaging signal output from the image sensor into an optical signal and to output the optical signal;

a first optical fiber configured to transmit the optical signal output from the light source;

a first optical connector configured to hold an end of the first optical fiber connected with the light source, the end being opposite to an end connected with the light source;

a second optical connector removably connected with the first optical connector;

a communication mode stabilizing unit provided between the transmission module and the first optical connector, the communication mode stabilizing unit being configured to transmit an output optical beam in the first optical fiber to the first optical connector so as to increase an amount of the output optical beam in a core of the first optical fiber as compared to an amount of an input optical beam in the core of the first optical fiber that is input into the communication mode stabilizing unit from the transmission module;

a second optical fiber configured to transmit the optical signal output from the first optical fiber, the second optical fiber being held by the second optical connector and having a core diameter larger than a core diameter of the first optical fiber;

a reception module including a sensor configured to convert the optical signal transmitted by the second optical fiber into an electrical signal and output the electrical signal;

a first correction optical system including a first lens incorporated in the first optical connector and configured to increase a beam diameter of the optical signal output from the end of the first optical fiber, and a second lens configured to convert the optical signal whose beam diameter is increased by the first lens into parallel light; and a second correction optical system including at least a third lens, the second correction optical system being incorporated in the second optical connector and configured to collect the optical signal output from the first correction optical system, wherein the second optical fiber is a step index optical fiber having a refractive index discontinuously changing only at a core-cladding interface.

2. The endoscope system according to claim 1, wherein the second optical fiber is a multicore fiber.

3. The endoscope system according to claim 2, wherein the second optical fiber is a multicore fiber including a plurality of cores having same diameter as a core of the first optical fiber.

4. The endoscope system according to claim 1, wherein the reception module includes a third correction optical system including at least a fourth lens, the second correction optical system being configured to collect the optical signal output from an end of the second optical fiber.

5. The endoscope system according to claim 1, wherein an end of the second optical fiber is an optical collecting part in a tapered shape, a hemispherical shape, a spherical shape or a wedge shape to collect the optical signal output to the reception module.

* * * * *